US00PP11143P

United States Patent [19]

Walden

[11] Patent Number: Plant 11,143

[45] Date of Patent: Dec. 7, 1999

[54] FLORIBUNDA ROSE PLANT NAMED 'JACMELLO'

[75] Inventor: John K. Walden, Thousand Oaks, Calif.

[73] Assignee: Bear Creek Gardens, Inc., Medford, Oreg.

[21] Appl. No.: 09/081,831

[22] Filed: May 19, 1998

[51] Int. Cl.[6] ..... A01H 5/00

[52] U.S. Cl. ..... Plt./145

[58] Field of Search ..... Plt./125, 145, 118

*Primary Examiner*—Howard J. Locker

*Attorney, Agent, or Firm*—Klarquist Sparkman Campbell Leigh & Whinston, LLP

[57] ABSTRACT

Floribunda rose plant having deep yellow flower color; dark green and glossy foliage; resistance to powdery mildew; upright, spreading plant habit; and ability to produce mature plants from softwood cuttings in pots in sixteen to eighteen week production cycle.

1 Drawing Sheet

The present invention relates to a new and distinct variety of rose plant of the floribunda class which was originated by me by crossing the variety JACyim, U.S. Plant Pat. No. 7,127, with AROyumi, U.S. Plant Pat. No. 5,703.

The primary objective of this breeding was to produce a new rose variety having a deep yellow flower color, dark green, disease resistant foliage, an upright plant habit suitable for pot forcing in a greenhouse and grown from softwood cuttings. The objective was substantially achieved, along with other desirable improvements, as evidenced by the following unique combination of characteristics that are outstanding in the new variety and that distinguish it from its parents, as well as from all other varieties of which I am aware:

1. Deep yellow flower color;
2. Dark green and glossy foliage;
3. Resistance to powdery mildew;
4. Upright and spreading plant habit; and
5. Ability to produce mature plants from softwood cuttings in pots in sixteen to eighteen week production cycle.

The variety 'JACmello' produces in sixteen to eighteen weeks a mature pot rose from softwood cuttings rooted directly in nursery containers and grown in a greenhouse.

Asexual reproduction of this new variety by softwood cuttings, as performed at Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—JACyim (U.S. Plant Pat. No. 7,127).

*Pollen Parent*.—AROyumi (U.S. Plant Pat. No. 5,703).

Classification:

*Botanical*.—Rosa hybrida

*Commercial*.—Floribunda

FLOWER

Observations made from specimens grown in a greenhouse environment at Somis, Calif. in February 1998.

Blooming habit: Recurrent.

Bud:

*Size*.—About ¾ to ⅞ inch long when the petals start to unfurl.

*Form*.—Short, pointed ovoid.

*Color*.—When sepals first divide, bud color is Yellow Group 12A. When half blown, the upper and lower sides of the petals are Yellow Group 6A.

*Sepals*.—Color: Close to Green Group 137C. Surface texture: Smooth to lightly hairy. There are three normally appendaged sepals. There are two unappendaged sepals with hairy and glandular edges.

*Receptacle*.—Color: Yellow-Green Group 144A. Shape: Funnel. Size: Small (about ¼"×¼"). Surface: Smooth.

*Peduncle*.—Length: About 1½ inches. Surface: Glandular. Color: Between Yellow-Green Group 144A and 144B. Strength: Stiff, erect.

Bloom:

*Size*.—Medium. Average open diameter is about 2½ inches.

*Borne*.—Singly and in clusters of three to seven flowers having a rounded shape.

*Stems*.—Short (about 7½").

*Form*.—When first open: Quartered to cupped. Permanence: Outer petal edges curl slightly.

*Petalage*.—Number of petals under normal conditions: 40–50.

*Color*. —The upper sides of the petals are Yellow Group 7A. The reverse sides of the petals are Yellow Goup 6A. The base of each petal has Yellow Group 7A on top and Yellow Group 6A on reverse. The major color on the upper sides is Yellow Group 7A.

*Variegations*.—None.

*Discoloration*.—At the end of the first day: Yellow Group 7A. At the end of the third day: No change.

*Fragrance*.—Slight.

Petals:

*Texture*.—Leathery.

*Shape*.—Oval.

*Form*.—Flat to moderately quilled.

*Arrangement*.—Quartered to imbricated. Petaloids in the center: Many (8–12), small.

*Persistence*.—Petals drop off cleanly before drying.

*Lastingness*.—On the plant: Long (12 days). As a cut flower: 12–14 days.

Reproductive Parts:

*Anthers*.—Size: Medium. Quantity: Many. Color: Yellow. Arrangement: Regular around styles; some mixing with petaloids.

*Filaments*.—Color: Yellow.

*Pollen*.—Color: Gold yellow.

*Styles*.—Color: Near Yellow-Green Group 154D.

*Stigmas*.—Color: Greenish-white.

Plant:

*Form*.—Bush.

*Growth*.—Medium; upright. In the ground, at maturity, height is 24 inches, width is 20–24 inches.

Foliage:

Number of leaflets on normal mid-stem leaves: Five, occasionally seven.

*Size*.—Medium (4" long×2¾" wide).

*Quantity*.—Normal.

*Color*.—New foliage: Upper side: Green group 137A. Lower side: Yellow-Green Group 146B. Old foliage: Upper side: Near Green Group 137A. Lower side: Near Yellow-Green Group 147B.

Leaflets:

*Shape*.—Broadly oval.

*Texture*.—Leathery, glossy, smooth.

*Edge*.—Serrated.

*Serration*.—Single.

*Petiole rachis*.—Color: Reddish, quickly changing to green.

*Petiole underside*.—Smooth, with prickles.

*Stipules*.—Medium (½"), serrated.

*Disease resistance*.—Resistant to mildew under normal growing conditions at Somis, Calif.

Wood:

*New wood*.—Color: Light green with slight reddish, quickly changing to green, between Yellow-Green Group 146B and 146C. Bark: Smooth.

*Old wood*.—Color: Yellow-Green Group 146B. Bark: Smooth.

Prickles:

*Quantity*.—On main canes from base: Ordinary. On laterals from main canes: Ordinary.

*Form*.—Long, straight.

*Color when young*.—Near Greyed Red Group 178C.

*Color when mature*: Near Greyed Orange Group 165A.

Small Prickles:

*Quantity*.—On main stalks: None. On laterals: None.

I claim:

1. A new and distinct variety of rose plant of the floribunda class, as herein shown and described, characterized particularly by its deep yellow flower color; dark green and glossy foliage; resistance to powdery mildew; upright, spreading plant habit; and ability to produce mature plants from softwood cuttings in pots in sixteen to eighteen week production cycle.

* * * * *

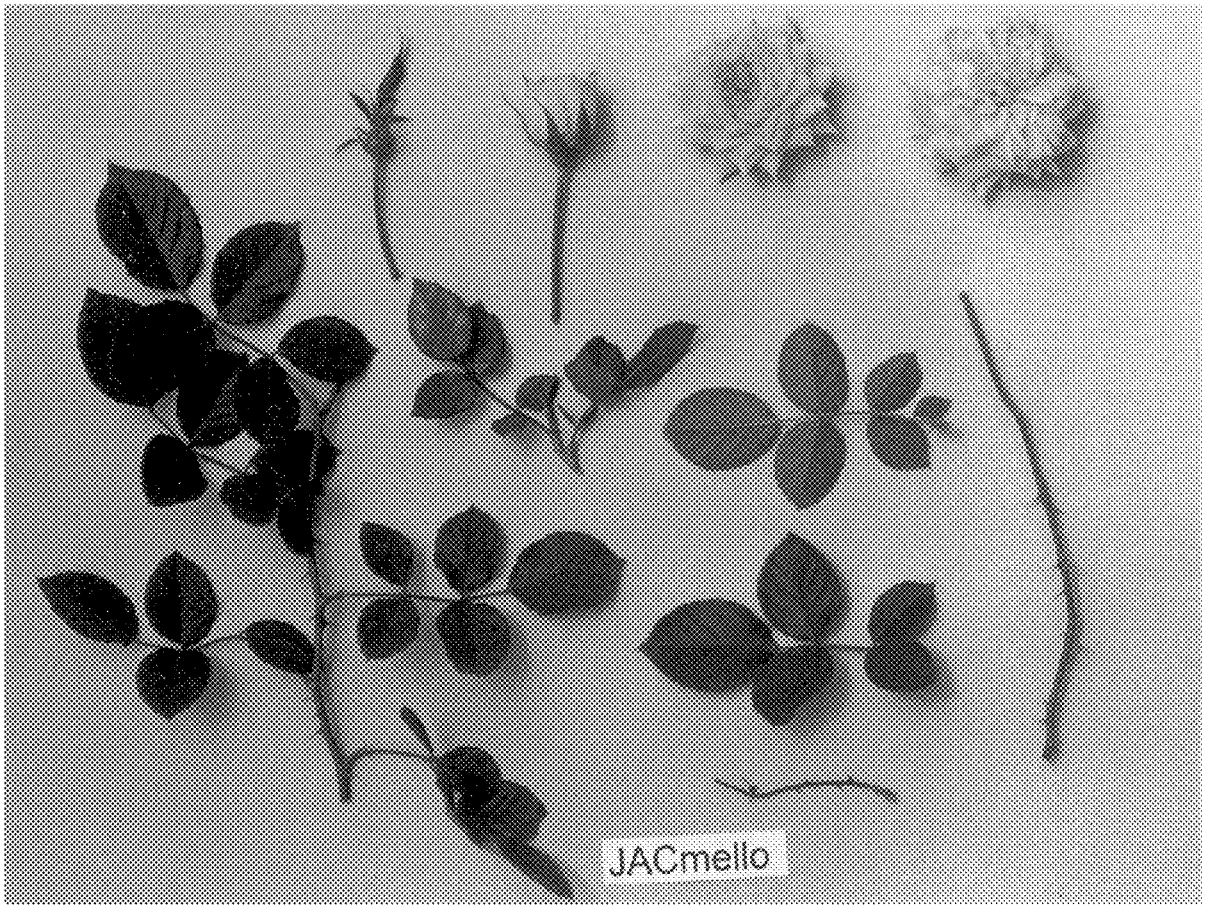
JACmello